United States Patent [19]

Wehner et al.

[11] 4,188,334
[45] Feb. 12, 1980

[54] ORGANOTIN COMPOUNDS

[75] Inventors: Wolfgang Wehner, Zwingenberg; Hermann O. Wirth, Bensheim, both of Fed. Rep. of Germany

[73] Assignee: Ciba-Geigy Corporation, Ardsley, N.Y.

[21] Appl. No.: 939,944

[22] Filed: Sep. 6, 1978

[30] Foreign Application Priority Data

Sep. 9, 1977 [CH] Switzerland .................. 11065/77

[51] Int. Cl.$^2$ .......................................... C07F 7/22
[52] U.S. Cl. ............................ 260/429.7; 260/45.75 H
[58] Field of Search .................................. 260/429.7

[56] References Cited

U.S. PATENT DOCUMENTS

| | | | |
|---|---|---|---|
| 3,347,890 | 10/1967 | Davies | 260/429.7 |
| 3,440,255 | 4/1969 | Matsuda et al. | 260/429.7 |
| 3,607,893 | 9/1971 | Reifenberg | 260/429.7 |
| 4,080,362 | 3/1978 | Hutton et al. | 260/429.7 X |
| 4,080,363 | 3/1978 | Hutton et al. | 260/429.7 X |
| 4,105,684 | 8/1978 | Hutton et al. | 260/429.7 |

OTHER PUBLICATIONS

Chemical Abstracts 68 59672c (1968).

Chemical Abstracts 68 87363w (1968).

*Primary Examiner*—Helen M. S. Sneed
*Attorney, Agent, or Firm*—Luther A. R. Hall

[57] ABSTRACT

Organotin compounds of the general formula

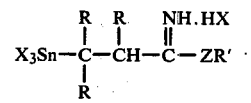

wherein
  X is a chlorine, bromine or iodine atom,
  R is a hydrogen atom and/or an alkyl radical,
  Z is an oxygen or sulfur atom, and
  R' is a hydrocarbon group of aliphatic, cycloaliphatic or aromatic character which can contain functional groups, and a process for their production by the direct reaction of a tin dihalide with an unsaturated nitrile.

The organotin compounds are used as intermediates for the production of organotin stabilizers for halogen-containing thermoplastics.

6 Claims, No Drawings

ORGANOTIN COMPOUNDS

The present invention relates to carbofunctional organotin compounds, a process for their manufacture and the use thereof.

Organotin compounds are of considerable economic importance as stabilisers for halogen-containing thermoplastics. Recently, carbofunctional organotin compounds have been proposed for this purpose. There are various possibilities of producing such stabilisers.

For example, German Offenlegungsschrift No. 1,963,569 discloses in general terms the reaction of halostannic acid with an olefin in the presence of a polar solvent. The olefin may contain functional groups and acrylonitrile is cited by way of example. However, it has been found that in this reaction the desired compound is obtained only in insufficient yield. Furthermore, undesired secondary reactions occur.

Monoorganotin compounds can also be obtained by a process disclosed in German Offenlegungsschrift No. 2,540,210. These compounds are obtained by reacting tin dihalide with hydrogen halide and a corresponding olefin. However, this process is restricted to those olefins which contain a carbonyl group in conjugation to the double bond and it cannot be generally applied to other substituted vinyl compounds, for example nitriles.

There is consequently a need for economic methods of producing monoorganotin derivatives using easily obtainable starting materials, and by means of which new compounds can also be obtained.

Accordingly, it is an object of the present invention to provide an economic process for producing new carbofunctional organotin compounds of the formula

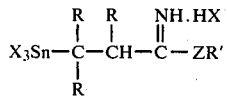

wherein
X is a chlorine, bromine or iodine atom,
R is a hydrogen atom and/or an alkyl radical,
Z is an oxygen or sulfur atom, and
R' is a hydrocarbon group of aliphatic, cyloaliphatic or aromatic character which can contain a functional group, by the direct reaction of a tin dihalide with an unsaturated nitrile of the formula

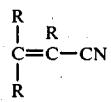

wherein R has the indicated meaning, and hydrogen chloride, bromide or iodide, which process comprises carrying out the reaction in the presence of an alcohol R'OH and, to produce the thioimino esters, reacting the imino esters with a mercaptan R'SH.

The organotin compounds of the given formula constitute a further object of the invention.

Substantially for economic reasons, X represents a chlorine atom. R is preferably hydrogen and/or methyl, especially hydrogen, this preference arising from the easily obtainable nitriles, namely acrylonitrile, methacrylonitrile, crotonitrile and β-dimethylacrylonitrile.

R' as a hydrocarbon group can be linear or branched alkyl, ubsubstituted or substituted cycloalkyl, cycloalkylalkyl, aryl and aralkyl, the preferred substituent being alkyl which can contain functional groups. Cycloalkyl is preferably cyclohexyl, aryl is phenyl and aralkyl is benzyl. R' preferably contains 1 to 12 carbon atoms and represents in particular cycloalkyl or linear or branched alkyl.

If R' is substituted by functional groups, such groups are for example hydroxyl, thiol, alkoxy, alkylthio, carboxyl and carbalkoxy.

Examples of R' are:
methyl, ethyl, n-propyl or isopropyl, n-butyl, isobutyl and tert-butyl, pentyl, hexyl, heptyl, 2-hexyl, 3-heptyl, octyl, 2-ethylhexyl, nonyl, decyl, undecyl, dodecyl, cyclopentyl, cyclohexyl, methylclohexyl, cyclohexylmethyl, methylcyclohexylmethyl, phenyl, methylphenyl, ethylphenyl, butylphenyl, octylphenyl, naphthyl, benzyl, methylbenzyl, octylbenzyl, α- or β-phenylethyl.

Examples of R' substituted by functional groups are:
β-hydroxyethyl, β-mercaptoethyl, methoxyethyl, butoxyethyl, octoxyethyl, methylthioethyl, propylthioethyl, carboxylmethyl, β-carboxylethyl, and carboalkoxyalkyl, i.e. carbomethoxymethyl, carboethoxypropyl, carbobutoxyethyl, carbododecyloxymethyl.

In the process of the present invention, the tin dihalide can be used in a number of different forms, for example as fused anhydrous salt, in the form of flakes or as dried salt in powder or dust form. It is also possible to carry out the reaction in an excess of reactants (alcohol and/or nitrile) or in an additional solvent. Suitable solvents in this connection are inert solvents, for example those with ether, carboxylic acid ester, keto or sulfone function, or hydrocarbons and halogenated hydrocarbons or acid amides, for example methylene chloride, chloroform, toluene or dimethyl formamide.

In the reaction of the invention it is essential that, in addition to the unsaturated nitrile, an alcohol is present preferably in at least molar ratio. This ratio can be about 1:1 to 1:1.2.

The raction temperature is in general from −30° to 100° C., preferably from 20° to 50° C. The reaction is advantageously carried out under normal pressure or slight excess pressure.

The procedure is that the reaction vessel is charged with the tin dihalide and the reactants, with or without solvent, and the hydrogen halide (preferably HCl) is introduced.

However, it is also possible to charge the reaction vessel with the tin dihalide in the solvent and to add the reactants and hydrogen chlorine gas simultaneously. In this case it is advantageous to proceed according to the countercurrent principle, by which means it is also possible to carry out the process continuously.

In a further embodiment of the process, the reaction can be carried out stepwise by first preparing trichlorostannate in a suitable solvent and subsequently reacting it with the unsaturated nitrile in the presence of an alcohol. The trichlorostannate can be obtained by treating tin dihalide or tin with hydrogen halide in polar solvents, especially ethers.

The reaction of the imino esters can be carried out in the same solvents as those referred to above. On occasion the mercaptan can also be used as solvent, in which case an excess is employed. Otherwise, stoichiometric ratios are preferred. The acid and basic catalysts conventionally employed for transesterification reactions can be used for this reaction, for example Lewis acids or alkali metal alcoholates.

However, the reaction can also be carried out without a catalyst. Preferably, the reaction is carried out in the presence of HCl (gaseous or dissolved). The imino esters do not need to be isolated before the reaction and the reaction mixture obtained during the first reaction can be used directly.

The process of the present invention surprisingly yields valuable new organotin compounds in simple manner, economically, in high yield and under very mild reaction conditions, whilst using readily obtainable and cheap raw materials as starting materials.

The organotin compounds of the invention are amorphous or crystalline, liquid or viscous or partially resinous substances which are colourless and partly water-soluble or soluble in organic solvents. They are pre-eminently suitable for use as active biocides. They are also suitable for use as catalysts or catalyst components for the production of polyurethane.

Finally, the compounds of the invention can be used as intermediates for the production of stabilisers for halogen-containing thermoplastics. For example, organotin compounds of the kind described in German Offenlegungsschrift No. 2,540,210 can be prepared by hydrolysis and can in turn be converted into stabilisers by the processes described therein. The invention is illustrated in more detail by the following Examples, in which the parts are by weight.

EXAMPLE 1

A three-necked flask equipped with stirrer, reflux cooler and bubble counter is charged at 20° C. with 37.9 parts of dry $SnCl_2$, 10.6 parts of acrylonitrile and 9.2 parts of absolute ethanol in 50 parts of dimethoxyethane. With stirring, a dry steam of HCl gas is passed through the mixture so that the temperature does not rise above 55° C. The reaction is complete after about 4 hours (HCl saturation). The clear reaction solution is freed from volatile constituents in vacuum. Virtually no $Sn^{2+}$ can be detected in the colourless residue. The $^1$NMR spectrum is in accordance with the following structure:

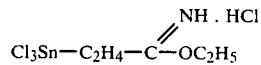

EXAMPLE 2

The reactants of Example 1 are reacted under the same condition in chloroform as solvent. After 4 hours a semifluid reaction mass is obtained, from which a colourless solid with a melting point of 130° C.-132° C. (with decomp.) can be isolated and the $^1$NMR spectrum of which is in accordance with that of Example 1. A $Sn^{2+}$ content of only 0.2% is measured by complexometric titration.

EXAMPLE 3

In the reaction of Example 2, the ethanol is replaced by 26.5 parts of n-butyl glycolate. The reaction is complete after 5 hours. The $^1$NMR spectrum shows the resulting compound to have the structure

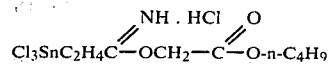

EXAMPLE 4

The reaction of Example 1 is repeated using 15.2 parts of glycolic acid in 200 parts of a 1:1 mixture of dimethoxyethane and $CHCl_3$ as solvent. The reaction time is 5 hours. The $^1$NMR spectrum shows the resulting compound to have the structure:

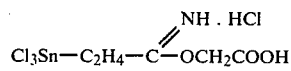

EXAMPLE 5

The reaction described in Example 2 is carried out with 18.8 parts of phenol instead of ethanol. After 3½ hours, a colourless solid which melts at 118° C.-120° C. with decomposition is obtained in 82% yield. The $^1$NMR spectrum is in accordance with the following structure:

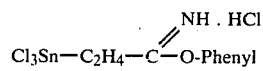

EXAMPLE 6

The reaction of Example 2 is repeated with 21.6 parts of benzyl alcohol. After a reaction time of 6 hours, the volatile constituents are removed, affording a colourless residue which the $^1$NMR spectrum shows to have the following structure:

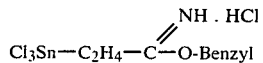

EXAMPLE 7

Following the procedure of Example 1, a reaction in the solvent mixture of Example 4 is carried out, replacing the ethanol by 6.2 parts of ethylene glycol (dried and distilled over a molecular sieve). After 5 hours a highly viscous residue is obtained. The $^1$NMR spectrum shows the compound to have the structure

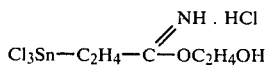

EXAMPLE 8 (COMPARISON EXAMPLE)

Following the procedure of Example 1, 37.9 parts of $SnCl_2$ and 10.6 parts of acrylonitrile in 70 parts of dimethoxyethane are reacted with HCl gas. After a reaction time of 4 hours, a light yellow solution is obtained in which $SnCl_4$ can be detected via an alkylation as (hexyl)$_4$Sn. Four substances can be detected in the NH range of the $^1$NMR spectrum. After a time, a product, in which 2 substances can be detected by $^1$NMR spectroscopy, crystallises from the solution. However, no $Cl_3SnC_2H_4CN$ is detectable in the IR spectrum.

EXAMPLE 9 (COMPARISON)

The reaction of Example 8 is repeated. After a reaction time of 7 hours, 9.2 parts of ethanol are added while introducing further HCl gas. After working up, it is not possible to detect any substance of Example 1, which should have resulted in the formation of $Cl_3SnC_2H_4CN$ as intermediate.

EXAMPLE 10

Production of

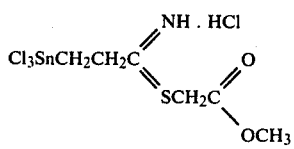

To 18.1 parts of the compound prepared according to Example 1 are added, in the same apparatus, 5.3 parts of methyl thioglycolate and 100 parts of dimethoxyethane. Then HCl gas is passed into the solution over the course of about 2 hours until saturation is attained. A small amount of precipitate is then collected by filtration and the volatile constituents are removed in vacuum. The residue is a light yellow, viscous oil, in which the title compound can be characterised as main constituent by $^1$NMR spectroscopy.

What is claimed is:

1. An organotin compound of the general formula

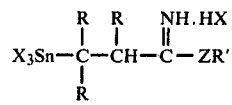

wherein
X is a chlorine, bromine or iodine atom,
R is selected from the group consisting of a hydrogen atom and alkyl,
Z is an oxygen or sulphur atom, and
R' is a hydrocarbon group of aliphatic, cycloaliphatic or aromatic character, or said group substituted by a hydroxyl, thiol, alkoxy, alkylthio, carboxyl or carboalkoxy group.

2. An organotin compound according to claim 1 wherein R is selected from the group consisting of a hydrogen atom and methyl.

3. An organotin compound according to claim 1 wherein R is a hydrogen atom.

4. An organotin compound according to claim 1 wherein X is a chlorine atom.

5. An organotin compound according to claim 1 wherein the hydrocarbon group R' contains 1 to 12 carbon atoms and is linear or branched alkyl or cycloalkyl.

6. Trichloro-(2-ethoxycarboximidoylethyl) tin hydrochloride.

* * * * *